(12) United States Patent
Greenhalgh et al.

(10) Patent No.: US 7,122,043 B2
(45) Date of Patent: Oct. 17, 2006

(54) TISSUE DISTENTION DEVICE AND RELATED METHODS FOR THERAPEUTIC INTERVENTION

(75) Inventors: E. Skott Greenhalgh, Wyndmoor, PA (US); Stephen J. Kleshinski, Scituate, MA (US)

(73) Assignee: Stout Medical Group, L.P., Perkasie, PA (US)

(*) Notice: Subject to any disclaimer, the term of this patent is extended or adjusted under 35 U.S.C. 154(b) by 0 days.

(21) Appl. No.: 10/847,909

(22) Filed: May 19, 2004

(65) Prior Publication Data

US 2005/0049681 A1    Mar. 3, 2005

Related U.S. Application Data

(60) Provisional application No. 60/471,555, filed on May 19, 2003.

(51) Int. Cl.
*A61M 29/00* (2006.01)

(52) U.S. Cl. .................. 606/191; 606/151; 606/194; 606/213

(58) Field of Classification Search ............. 606/108, 606/151, 213; 623/1.15, 1.2
See application file for complete search history.

(56) References Cited

U.S. PATENT DOCUMENTS

| | | | |
|---|---|---|---|
| 3,656,185 A | 4/1972 | Carpentier | |
| 3,874,388 A | 4/1975 | King et al. | |
| 4,007,743 A | 2/1977 | Blake | |
| 4,055,861 A | 11/1977 | Carpentier | |
| 4,306,319 A | 12/1981 | Kaster | |
| 4,917,089 A | 4/1990 | Sideris | |
| 4,957,501 A | 9/1990 | Lahille et al. | |
| 4,991,602 A | 2/1991 | Amplatz et al. | |
| 5,061,277 A | 10/1991 | Carpentier et al. | |
| 5,067,489 A | 11/1991 | Lind | |
| 5,104,407 A | 4/1992 | Lam et al. | |
| 5,171,259 A | 12/1992 | Inoue | |
| 5,234,458 A | 8/1993 | Metais | |
| 5,334,217 A * | 8/1994 | Das ........................ | 606/213 |
| 5,342,304 A | 8/1994 | Tacklind et al. | |
| 5,601,595 A | 2/1997 | Smith | |
| 5,634,931 A | 6/1997 | Kugel | |
| 5,716,397 A | 2/1998 | Myers | |
| 5,919,200 A | 7/1999 | Stambaugh et al. | |
| 5,944,738 A | 8/1999 | Amplatz et al. | |
| 5,972,030 A | 10/1999 | Garrison et al. | |
| 6,007,557 A | 12/1999 | Ambrisco et al. | |
| 6,093,199 A | 7/2000 | Brown et al. | |
| 6,126,673 A | 10/2000 | Kim et al. | |

(Continued)

OTHER PUBLICATIONS

Sievert, H. et al., Percutaneous Closure of 176 Inter-Artrial Defects in Adults with Different Occlusion Devices—6 Years of Experience (abstract), *J. Am. Coll. Cerdiol* 1999, 33:519A-520A.

(Continued)

*Primary Examiner*—Julian W. Woo
*Assistant Examiner*—Sarah Webb
(74) *Attorney, Agent, or Firm*—Levine Bagade Han LLP

(57) ABSTRACT

A device positionable in an opening in a flexible membrane or in the lumen of a vessel having a flexible sidewall. The device distends or biases opposite portions defining the opening or forming the vessel sidewall outwardly in the plane of the device. The outward biasing draws opposing portions of the opening or sidewall inwardly in a direction perpendicular to the plane of the device and into apposition or contact.

13 Claims, 15 Drawing Sheets

U.S. PATENT DOCUMENTS

| | | | |
|---|---|---|---|
| 6,143,024 A | 11/2000 | Campbell et al. | |
| 6,152,144 A | 11/2000 | Lesh et al. | |
| 6,152,947 A | 11/2000 | Ambrisco et al. | |
| 6,159,240 A | 12/2000 | Sparer et al. | |
| 6,168,616 B1 | 1/2001 | Brown, III | |
| 6,200,336 B1 * | 3/2001 | Pavcnik et al. | 623/1.15 |
| 6,206,907 B1 | 3/2001 | Marino et al. | |
| 6,231,561 B1 | 5/2001 | Frazier et al. | |
| 6,258,122 B1 | 7/2001 | Tweden et al. | |
| 6,267,777 B1 | 7/2001 | Bosma et al. | |
| 6,273,901 B1 | 8/2001 | Whicher et al. | |
| 6,290,674 B1 | 9/2001 | Roue et al. | |
| 6,312,447 B1 | 11/2001 | Grimes | |
| 6,319,268 B1 | 11/2001 | Ambrisco et al. | |
| 6,328,727 B1 | 12/2001 | Frazier et al. | |
| 6,332,892 B1 | 12/2001 | Desmond, III et al. | |
| 6,344,048 B1 | 2/2002 | Chin et al. | |
| 6,348,063 B1 | 2/2002 | Yassour et al. | |
| 6,402,771 B1 | 6/2002 | Palmer et al. | |
| 6,416,549 B1 | 7/2002 | Chinn et al. | |
| 6,419,669 B1 | 7/2002 | Frazier et al. | |
| 6,419,695 B1 | 7/2002 | Gabbay | |
| 6,468,290 B1 | 10/2002 | Weldon et al. | |
| 6,482,224 B1 | 11/2002 | Michler et al. | |
| 6,551,303 B1 | 4/2003 | Van Tassel et al. | |
| 6,558,404 B1 | 5/2003 | Tsukernik | |
| 6,652,555 B1 | 11/2003 | VanTassel et al. | |
| 6,652,556 B1 | 11/2003 | VanTassel et al. | |
| 6,673,089 B1 | 1/2004 | Yassour et al. | |
| 6,689,150 B1 | 2/2004 | VanTassel et al. | |
| 6,730,108 B1 | 5/2004 | Van Tassel et al. | |
| 6,740,112 B1 | 5/2004 | Yodfat et al. | |
| 6,939,348 B1 | 9/2005 | Malecki et al. | |
| 6,949,113 B1 | 9/2005 | Van Tassel et al. | |
| 6,994,092 B1 | 2/2006 | van der Burg et al. | |
| 2002/0022860 A1 | 2/2002 | Borillo et al. | |
| 2002/0077596 A1 | 6/2002 | McKenzie et al. | |
| 2003/0045898 A1 | 3/2003 | Harrison et al. | |
| 2003/0057156 A1 | 3/2003 | Peterson et al. | |
| 2003/0097145 A1 | 5/2003 | Goldberg et al. | |
| 2003/0120337 A1 | 6/2003 | Van Tassel et al. | |
| 2003/0144694 A1 | 7/2003 | Chanduszko et al. | |
| 2003/0153943 A1 | 8/2003 | Michael et al. | |
| 2003/0171803 A1 | 9/2003 | Shimon | |
| 2003/0181942 A1 | 9/2003 | Sutton et al. | |
| 2003/0181945 A1 | 9/2003 | Opolski et al. | |
| 2003/0187474 A1 | 10/2003 | Keegan et al. | |
| 2003/0191495 A1 | 10/2003 | Ryan et al. | |
| 2003/0191526 A1 | 10/2003 | Van Tassel et al. | |
| 2003/0195553 A1 | 10/2003 | Wallace et al. | |
| 2003/0212429 A1 | 11/2003 | Keegan et al. | |
| 2003/0220667 A1 | 11/2003 | van der Burg et al. | |
| 2003/0225421 A1 | 12/2003 | Peavey et al. | |
| 2003/0225453 A1 * | 12/2003 | Murch | 623/1.21 |
| 2004/0034366 A1 | 2/2004 | van der Burg et al. | |
| 2004/0049226 A1 | 3/2004 | Keegan | |
| 2004/0073242 A1 | 4/2004 | Chanduszko | |
| 2004/0087968 A1 | 5/2004 | Core | |
| 2004/0092973 A1 | 5/2004 | Chanduszko et al. | |
| 2004/0098031 A1 | 5/2004 | van der Burg et al. | |
| 2004/0098121 A1 | 5/2004 | Opolski | |
| 2004/0133236 A1 | 7/2004 | Chanduszko | |
| 2004/0153135 A1 | 8/2004 | Haase et al. | |
| 2004/0167566 A1 | 8/2004 | Beulke et al. | |
| 2004/0167613 A1 | 8/2004 | Yodfat et al. | |
| 2004/0176788 A1 | 9/2004 | Opolski | |
| 2004/0176797 A1 | 9/2004 | Opolski | |
| 2004/0176799 A1 | 9/2004 | Chanduszko et al. | |
| 2004/0181253 A1 | 9/2004 | Sepetka et al. | |
| 2004/0193147 A1 | 9/2004 | Malecki et al. | |
| 2004/0220596 A1 | 11/2004 | Frazier et al. | |
| 2004/0230185 A1 | 11/2004 | Malecki et al. | |
| 2004/0267191 A1 | 12/2004 | Gifford, III et al. | |
| 2005/0021016 A1 | 1/2005 | Malecki et al. | |
| 2005/0034735 A1 | 2/2005 | Deem et al. | |
| 2005/0043759 A1 | 2/2005 | Chanduszko | |
| 2005/0049573 A1 | 3/2005 | Van Tassel et al. | |
| 2005/0085843 A1 | 4/2005 | Opolski et al. | |
| 2005/0085848 A1 | 4/2005 | Johnson et al. | |
| 2005/0101984 A1 | 5/2005 | Chanduszko et al. | |
| 2005/0101987 A1 | 5/2005 | Salahieh | |
| 2005/0192620 A1 | 9/2005 | Cully et al. | |
| 2005/0192626 A1 | 9/2005 | Widomski et al. | |
| 2005/0192654 A1 | 9/2005 | Chanduszko et al. | |
| 2005/0203567 A1 | 9/2005 | Linder et al. | |
| 2005/0203568 A1 | 9/2005 | van der Burg et al. | |
| 2005/0209636 A1 | 9/2005 | Widomski et al. | |
| 2005/0251157 A1 | 11/2005 | Chanduszko et al. | |
| 2005/0267523 A1 | 12/2005 | Devellian et al. | |
| 2005/0267524 A1 | 12/2005 | Chanduszko | |
| 2005/0267525 A1 | 12/2005 | Chanduszko | |
| 2005/0273119 A1 | 12/2005 | Widomski et al. | |
| 2005/0273124 A1 | 12/2005 | Chanduszko | |
| 2005/0273135 A1 | 12/2005 | Chanduszko et al. | |
| 2005/0286706 A1 | 12/2005 | Widomski et al. | |
| 2005/0288786 A1 | 12/2005 | Chanduszko | |
| 2006/0009799 A1 | 1/2006 | Kleshinski et al. | |
| 2006/0015138 A1 | 1/2006 | Gertner | |
| 2006/0052821 A1 | 3/2006 | Abbott et al. | |
| 2006/0058833 A1 | 3/2006 | VanCamp et al. | |

OTHER PUBLICATIONS

Rao, P. S., Summary and Comparison of Atrial Septal Defect Closure Devices, *Current Interventional Cardiology Reports*, 2000, 2:367-376.

Rigby, M. L., The era of transcatheter closure of atrial septal defects, *Heart*, 1999, 81:227-228.

Sievert, H. et al., Percutaneous closure of 176 interarterial defects in adults with different occlusion devices—6 years of experience (abstract), *J. Am. Coll. Cardial*, 1999, 33:519A.

Rao, P. S., Summary and Comparison of Atrial Septal Defect Closure Devices, *Current Interventional Cardiology Reports*, 2000, 2:367-76.

Rigby, Michael L., The Era of Transcatheter Closure of Atrial Septal Defects, *Heart*, 1999, 81:227-228.

* cited by examiner

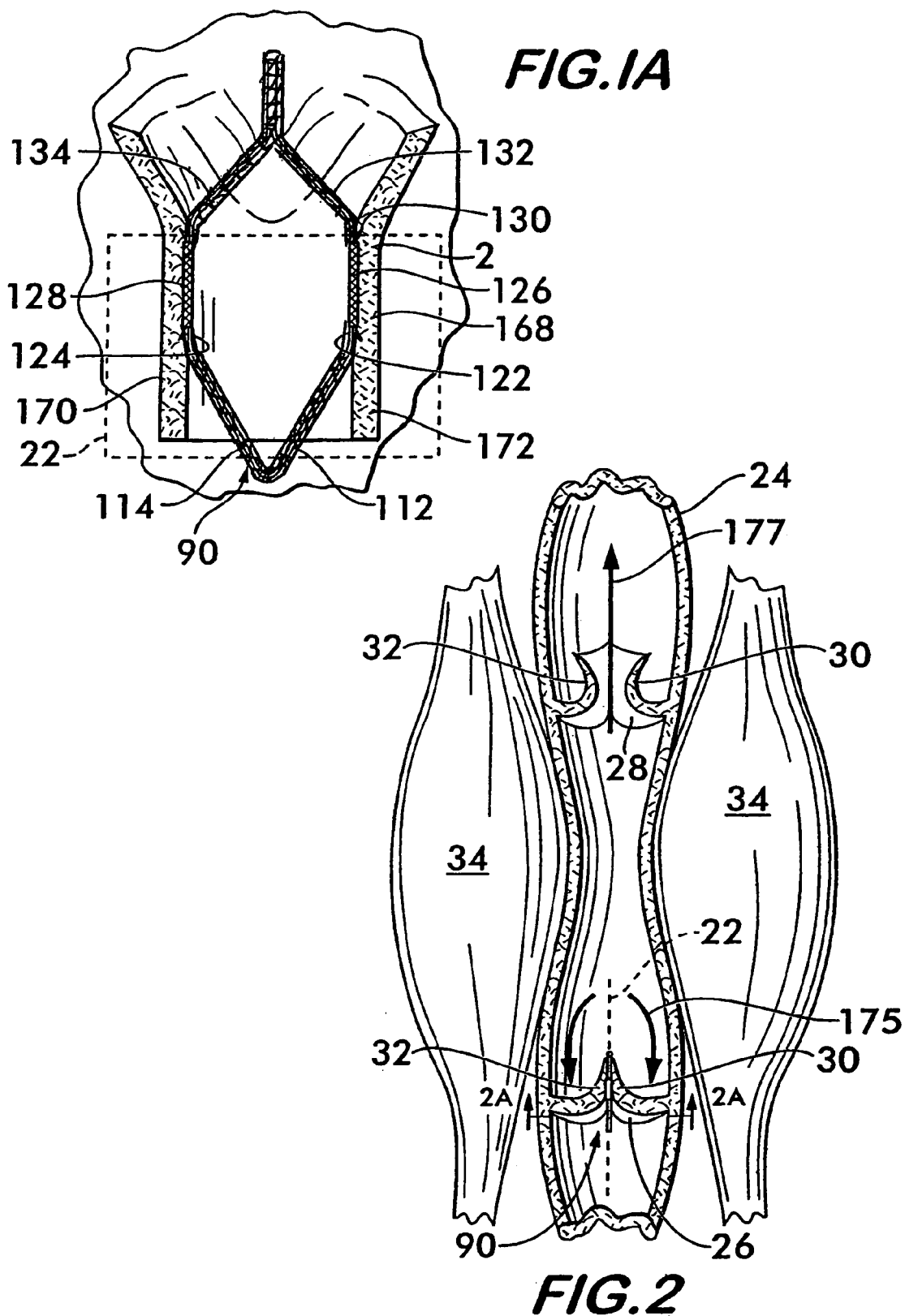

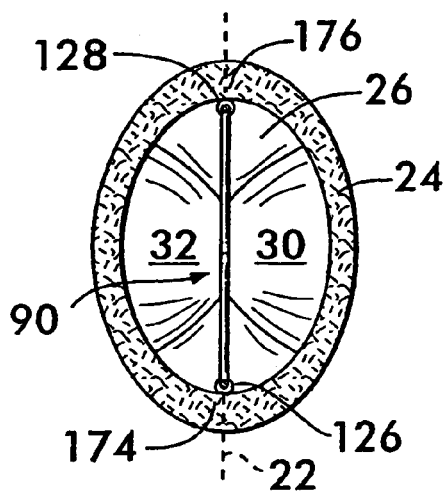
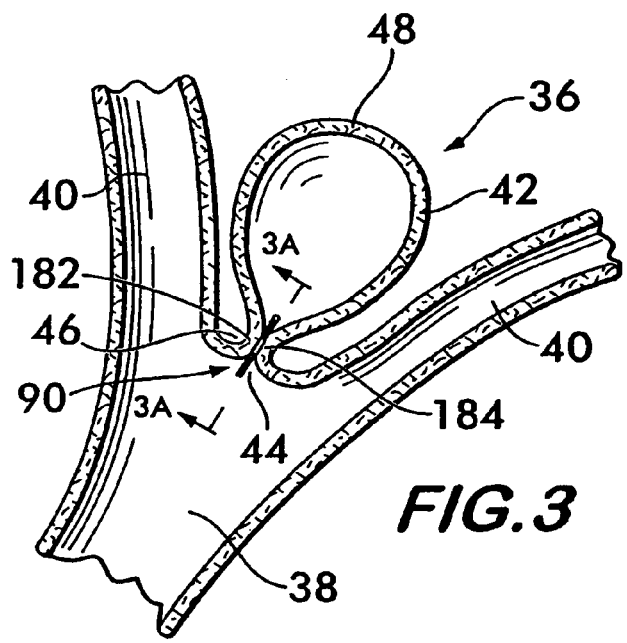
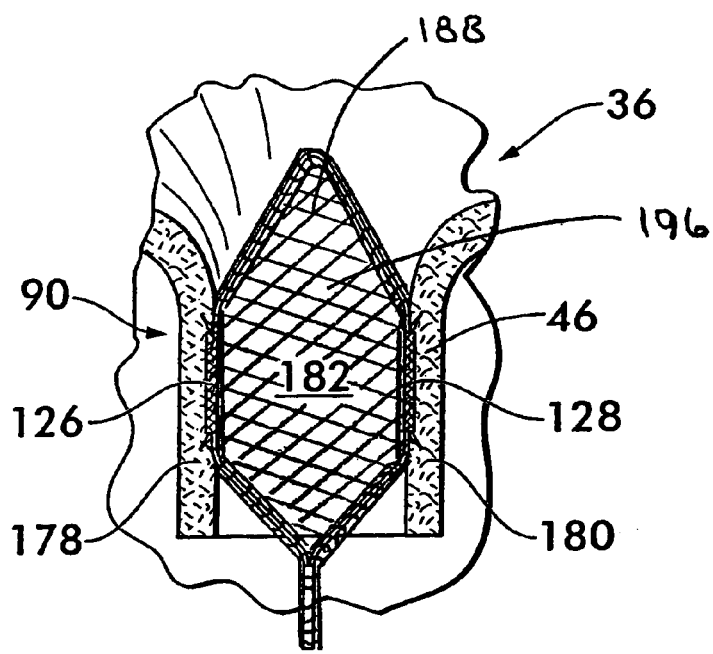

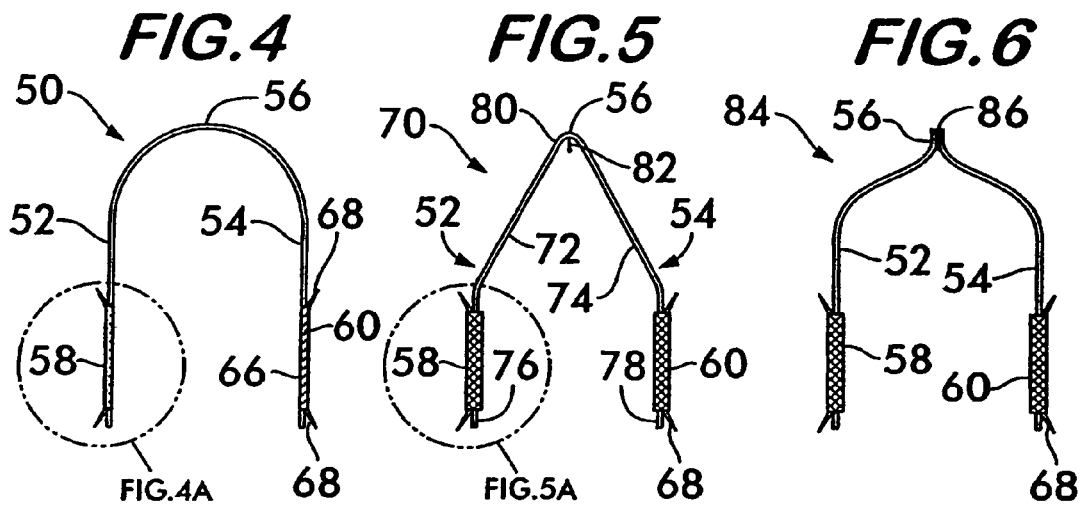
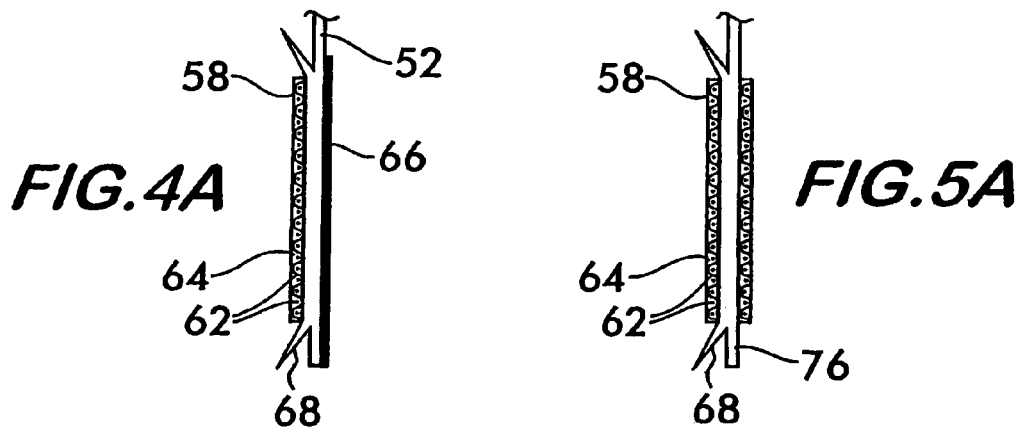
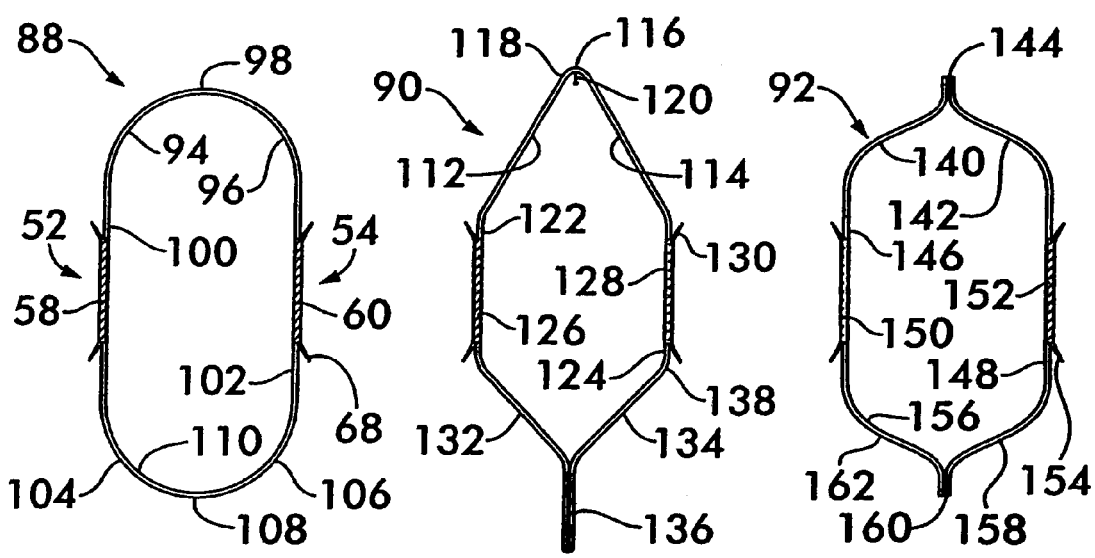

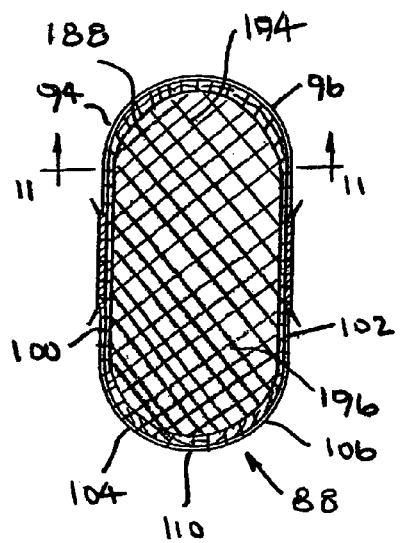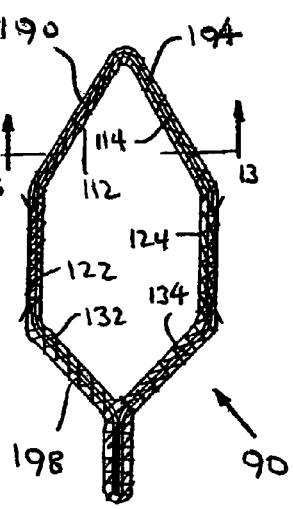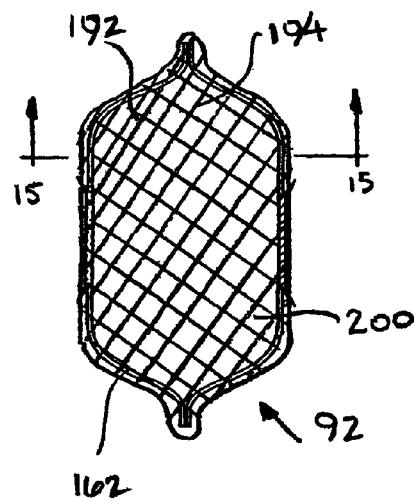
FIG 10    FIG 12    FIG 14
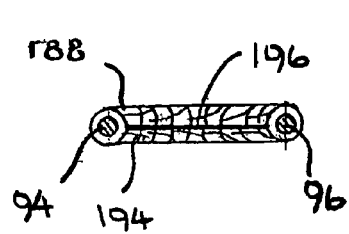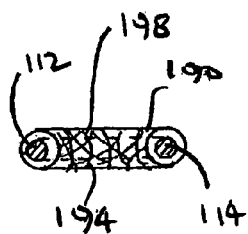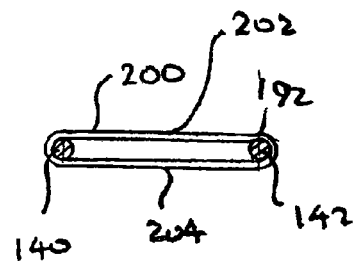
FIG 11    FIG 13    FIG 15

TISSUE DISTENTION DEVICE AND RELATED METHODS FOR THERAPEUTIC INTERVENTION

CROSS-REFERENCE TO RELATED APPLICATIONS

This application is based upon and claims priority to U.S. Provisional Patent No. 60/471,555 filed May 19, 2003, the entire disclosure of which is hereby incorporated by reference.

BACKGROUND OF THE INVENTION

1. Field of the Invention

This invention concerns a device positionable in an opening in a flexible membrane or in the lumen of a vessel having a flexible sidewall. The device distends or biases opposite portions defining the opening or forming the vessel sidewall outwardly in the plane of the device. The outward biasing draws opposing portions of the opening or sidewall inwardly in a direction perpendicular to the plane of the device and into apposition or contact.

2. Description of Related Art

Elastic membranes, in particular, living tissue such as muscular tissue, may be subject to defects, disorders or diseases wherein unwanted openings or cavities are formed through or in the tissue. Elastic vessels having flexible sidewalls are found extensively throughout the human body and perform a variety of vital functions, for example, carrying and distributing blood to tissue and transporting waste matter from the digestive and urinary systems. The vessels may use sphincters to control the flow of matter through the vessels or they may incorporate one-way valves to prevent back flow of fluid. The valves and even the vessels themselves may suffer from defects, disorders or abnormalities which inhibit their ability to function properly. Examples of various disorders of important muscular tissue as well as blood vessels are described below by way of specific examples.

Mitral Valve Incompetence

As shown in FIG. 1, the left atrioventricular or mitral valve 2 is a bicuspid (two-leaflet) valve positioned in the orifice 4 between the left atrium 6 and left ventricle 8 of the heart 10. Oxygen rich blood 12 flows from the lungs via pulmonary veins 14 to the left atrium 6, past the mitral valve 2 and into the left ventricle 8 where it is pumped to the aorta 16 for further distribution to the body. The mitral valve 2 has leaflets 18 and 20 in apposition to one another defining the plane 22 of the valve parallel to and between the leaflets. The mitral valve 2 is a one way valve, its leaflets 18 and 20 moving perpendicularly to the valve plane 22 away from one another to permit flow into the left ventricle 8, and closing against one another (also known as coaptation) in response to a pressure increase in the left ventricle 8 caused when it contracts to pump the blood through the aorta 16. In a healthy valve, the leaflets 18 and 20 normally seal against each other (coapt) to prevent back flow of blood through the left atrium 6 to the lungs. However, in a diseased mitral valve the leaflets may prolapse into the left atrium and allow a back flow of blood.

Of the various valves in the heart, the mitral valve is most vulnerable to disease and suffers from atrioventricular valvular incompetence whereby the mitral valve seals incompletely. This allows blood to regurgitate into the left atrium upon contraction of the left ventricle. The diseased leaflets of the valve undergo scarring and shortening which are one cause the valvular incompetence. Other causes include abnormal elongation of the chordae tendineae (tendinous cords attached to the free edges of the leaflets to prevent prolapse), as well as rigidity, deformity and retraction of the leaflets associated with rheumatic heart disease.

Due to the low success rate associated with mitral valve replacement, atrioventricular valvular incompetence is preferably treated by mitral valve repair requiring open heart surgery. This treatment is extremely invasive, requires that the heart be stopped and the patient put on cardiopulmonary bypass and often leads to post-operative complications.

Venous Valve Incompetence

As shown in FIG. 2, the veins 24 of the human circulatory system have a system of one-way valves such as 26 and 28, also comprising two leaflets 30 and 32, which operate to promote the flow of blood from the extremities back to the heart by preventing the retrograde flow of blood to the extremities between heart beats. The venous valves 26 and 28 also cooperate to allow muscular action to assist in the pumping of blood from the venous side of the circulatory system back to the heart. The contraction of various muscles 34 tends to constrict the veins 24, forcing blood to flow out of the vein, and the venous valves 26 and 28 cooperate, with valve 28 opening while valve 26 remains closed, to permit only one-way flow back to the heart.

The veins are subject to various disorders related to defective structure and function of their valves, known as valve incompetence. Valve incompetence can cause varicose veins, as well as chronic venous insufficiency wherein the valve leaflets become thickened and contracted so that they become incapable of preventing the retrograde flow of blood. Both of these conditions cause considerable discomfort and can lead to further complications such as edema, erythema, dermatitis, skin ulceration and cellulitis.

Arterial Saccular Aneurysms

As illustrated in FIG. 3, saccular aneurysms 36 occur at the branching 38 of arteries 40 in the body and comprise a sack-like formation of the artery wall 42 which extends outwardly from the bifurcation point 44 between the arterial branches 40. The aneurysm 36 has a neck 46 of reduced diameter forming the juncture with the artery 40 and is capped by a dome 48. During formation of the aneurysm 36, the arterial internal elastic lamina disappears at the neck 46, the wall 42 thins and weakens and connective tissue replaces smooth-muscle cells. The aneurysm tends to rupture at the dome 48 and bleeding ensues.

Rupture of a cerebrovascular saccular aneurysm is especially serious due to the associated high mortality rate (10% within the first day of rupture, 25% within three months) and the major neurological deficits experienced by those who survive the initial hemorrhage.

Patent Foramen Ovale

As shown in FIG. 1, the foramen 3 is an opening in the muscle tissue of the heart between the left and right atria (6 and 7 respectively). This opening is present before birth to allow blood to be channeled between the mother and the fetus. After birth the foramen normally closes to separate the atria and allow blood to be pumped by the infant's heart. Patent foramen ovale is a heart defect wherein the foramen fails to close after birth and allows leakage of blood between the atria. This defect results in a greater risk of pulmonary embolism and stroke.

Atrial Appendage

FIG. 1B is a partial sectional view taken at line 1B—1B in FIG. 1 and illustrates an atrial appendage 5 extending from the left atrium 6 adjacent to the pulmonary trunk 9. The atrial appendage 5 is approximately the size of a human thumb and performs no known useful function. It is, however, responsible for the formation of blood clots, and is believed to be responsible for 90 percent of strokes associated with non-rheumatic atrial fibrillation, or irregular heart beat. The risk of stroke is greatly reduced by closing off the atrial appendage 5 from the left atrium 6.

Atrial and Ventricular Septal Defects

An atrial septal defect, illustrated in FIG. 1C, is a heart defect characterized by an opening 13 in the septum or wall 15 separating the left and right atria 6 and 7 respectively. Similarly, a ventricular septal defect is characterized by an opening 17 in the septum 19 separating the left and right ventricles 8 and 11 respectively. Such openings allow blood to flow between the atria or the ventricles.

If untreated, an atrial septal defect places stress on the right ventricle which may dilate and weaken in response. The lungs may become congested and pulmonary hypertension may also result, as well as arrhythmias and blood clots leading to stroke. A ventricular septal defect also places greater stress on the right ventricle, again leading to congestion, pulmonary hypertension, blood clots, stroke and arrhythmia.

There is a need, therefore, for a device and a method which can be used to correct disorders and abnormalities associated with opening in muscular tissue as well as vessels having flexible, elastic sidewalls and which may be employed in a safe, minimally invasive manner to reduce trauma to the patient and minimize post-operative complications.

SUMMARY OF THE INVENTION

The invention concerns a biasing device positionable within an opening in a membrane such as muscle tissue or within a lumen of a vessel having a flexible sidewall. The device biases first opposing sidewall portions in a plane of the device outwardly away from one another while drawing second opposing sidewall portions toward one another in a direction substantially perpendicular to the plane of the device. The biasing device is insertable within the opening or lumen through a catheter. In one preferred embodiment, the device comprises a pair of resilient, flexible legs extending from a common end point. The legs are resiliently deformable between a first configuration wherein they are positioned proximate to one another so as to slidingly interfit within the catheter, and a second configuration wherein they are positioned in spaced relation to one another.

First and second anchoring substrates are preferably positioned lengthwise along each of the legs distally to the common end point. The anchoring substrates are formed from a plurality of filamentary members attached to the legs. The anchoring substrates define a plurality of interstices between the filamentary members. The anchoring substrates on each of the legs engage the first opposing sidewall portions when the legs are in the second configuration within the vessel, the legs biasing the first opposing sidewall portions outwardly and thereby drawing the second opposing sidewall portions inwardly.

In another embodiment, the invention comprises a pair of resilient, flexible legs having opposite ends joined to one another at first and second common end points thereby forming a closed loop. The legs are resiliently deformable between a first configuration, wherein the legs are positioned proximate to one another so as to slidingly interfit within the catheter, and a second configuration, wherein the legs are positioned in spaced relation to one another.

First and second anchoring substrates are preferably positioned opposite one another across the loop lengthwise along the legs. The anchoring substrates are again formed from a plurality of filamentary members attached to the legs, the filamentary members defining a plurality of interstices. The anchoring substrates on each of the legs engage the first opposing sidewall portions when the legs are in the second configuration within the vessel. The legs bias the first opposing sidewall portions outwardly and thereby draw the second opposing sidewall portions inwardly.

The device according to the invention also includes a shroud that covers the leg segments and may also provide a central layer spanning the space between the leg segments. The shroud is preferably formed from interlaced filamentary members and provides a matrix promoting the ingrowth of living tissue to secure the device to the tissue as well as provide a substrate for attaching tissue to tissue to permanently seal a vessel or opening.

The invention also includes a method of treating defects and disorders including patent foramen ovale, an atrial appendage, atrial and ventricular septal defects, a regurgitating mitral valve, a leaking venous valve, a saccular aneurysm or any disorder involving a vessel having a flexible sidewall by using a biasing device according to the invention. The steps of the method include:

(A) positioning the legs of the biasing device within the vessel or opening, for example in the opening plane of a valve, in the neck of a saccular aneurysm or in an opening between the left and right atria; and (B) biasing the legs into spaced relation with one another, the legs biasing first opposing portions of the vessel or opening outwardly and thereby drawing the opposing sidewall portions toward one another into apposition, for example, the leaflets of the valve, the neck portion of the aneurysm or the facing side portions defining the opening.

When treating a valve, the legs are positioned co-planarly with the plane of the valve. When anchoring substrates are present, the method includes the further step of engaging the anchoring substrates with first opposing portions of the opening or vessel, the device being positioned in the opening plane of the valve or the neck of the saccular aneurysm.

In one aspect, the invention provides a device for biasing opposing wall portions of an opening or a vessel into apposition.

In another aspect, the invention provides a device for controlling the flow of fluid or other matter through a vessel.

In yet another aspect, the invention provides a device for stopping the flow of fluid through a vessel or an opening.

In another aspect, the invention to provide a device for sealing an opening or vessel by promoting a healing reaction between portions of the vessel or wall portions defining the opening.

In yet another aspect, the invention provides a device that can be implanted in the human body through minimally invasive techniques.

In another aspect, the invention provides a device that can be used to correct mitral valve incompetence.

In another aspect, the invention provides a device that can be used to correct venous vein incompetence.

In yet another aspect, the invention provides a device that can be used to treat saccular aneurysms.

In a further aspect, the invention provides a device that can be used to correct patent foramen ovale.

In another aspect, the invention provides a device that can be used to correct atrial and ventricular septal defects.

It another aspect, the invention provides a device that can be used to close an atrial appendage.

In yet a further aspect, the invention provides a method of biasing opposing wall portions of a vessel or opening into apposition.

It another aspect, the invention provides a method for controlling the flow of a fluid through a vessel.

These and other objects and advantages of the invention will become apparent upon consideration of the drawings and the detailed description of preferred embodiments.

BRIEF DESCRIPTION OF THE DRAWINGS

FIG. 1A is a sectional view taken at line 1A—1A of FIG. 1 and illustrating a biasing device according to the invention positioned within the plane of the mitral valve;

FIG. 2 is a partial sectional view of a vein of a circulatory system;

FIG. 2A is a cross-sectional view taken at line 2A—2A of FIG. 2 and showing a biasing device according to the invention positioned within a venous valve;

FIG. 3 is a sectional view of a bifurcated artery with a saccular aneurysm;

FIG. 3A is a sectional view taken at line 3A—3A of FIG. 3 showing a biasing device according to the invention positioned within the neck of the saccular aneurysm;

FIGS. 4 through 9 are plan views of various embodiments of a biasing device according to the invention;

FIGS. 4A and 5A are plan views on an enlarged scale taken at broken circles 4A and 5A in FIGS. 4 and 5 respectively showing design details of the devices;

FIGS. 10, 12 and 14 are plan views of various embodiments of a biasing device according to the invention;

FIGS. 11, 13 and 15 are cross-sectional views of the various embodiments of the biasing devices taken at lines 11—11, 13—13 and 15—15 of FIGS. 10, 12 and 14 respectively;

DETAILED DESCRIPTION OF THE PREFERRED EMBODIMENTS

Figure 1:
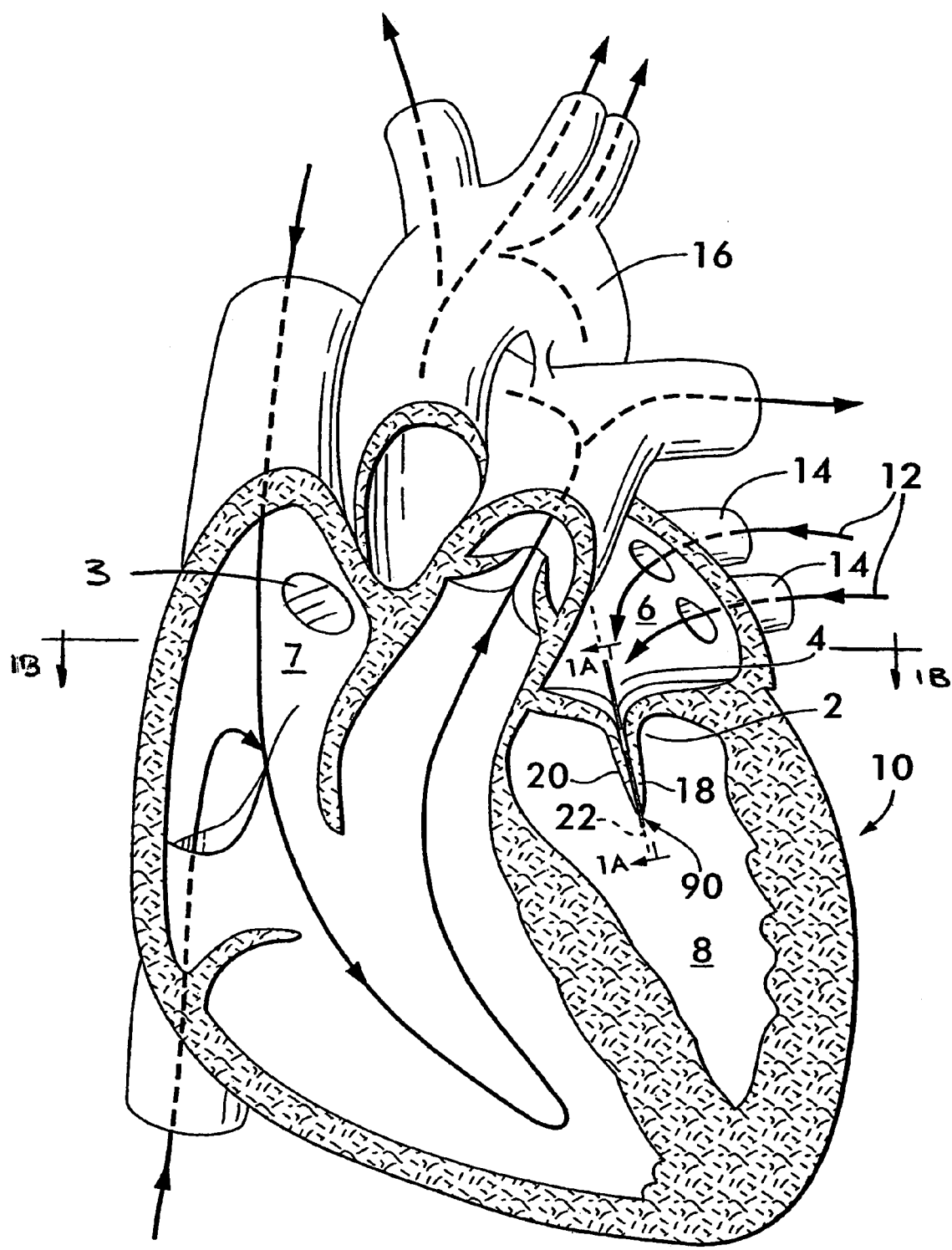
FIG. 1 is a partial sectional view through a human heart highlighting the left atrium, the left ventricle and the mitral valve controlling blood flow between them.

FIG. 4 shows an embodiment of a biasing device 50 according to the invention. Biasing device 50 comprises a pair of resilient, flexible legs 52 and 54 extending from a common end point 56. Legs 52 and 54 are preferably formed from a metal compatible with living tissue and having a relatively high yield stress, such as nitinol to provide the resilient biasing characteristics for proper functioning of the device as explained below. Other metals such as stainless steel, titanium and elgiloy are also feasible. Polymers such as polyester, polypropylene, and polytetrafluoroethylene may also be used to form the legs.

Anchoring substrates 58 and 60 are positioned lengthwise along a portion of each leg 52 and 54 distally to the common end point 56. As shown in detail in FIG. 4A, the anchoring substrates such as 58 (and 60, not shown in detail) are formed from filamentary members 62, preferably interlaced by braiding to form interstices 64 between the filamentary members 62. The denier of the filamentary members 62 and the density of the interlacing are controlled so as to produce interstices 64 sized to promote the intergrowth of living tissue into the anchoring substrates 58 and 60, thereby organically attaching the device 50 to the sidewalls of the vessel in which it is inserted. Presently, polyester monofilaments having a denier of 60 and braided at 120 picks per inch are preferred, yielding interstices having dimensions on the order of 0.004 inches across. Multifilament polyester of 60 denier may also be used to create a more compliant covering. This is useful when space is limited, such as during delivery of the device.

To further promote cellular growth, the filamentary members may be coated with thrombin, collagen, hyaluron or a host of growth factors such as VEGf which promote blood clotting or integration of inert material with living tissue. Furthermore, the rest of the device may be coated with antiproliferative drugs, such as Taxol, Rapamycin, Rapamune, to act as a barrier to all proliferation and be a deterrent to adhesion of living tissue where it is not desired.

Polyester is a preferred material for the filamentary members 62 in view of its long term successful use in human implants. Other polymer materials which are also feasible include polypropylene, polytetrafluoroethylene and nylon. Metals may also be used to form the filamentary members, in particular, gold is preferred due to its compatibility with human tissue and its high degree of radiopacity. Gold filaments, either comprising the filamentary members or being interlaced among them serve as a radiopaque marker allowing fluoroscopic and x-ray techniques to be used to view the position and orientation of the device 50 during and after implantation. Gold coatings 66 may also be applied to the filamentary members 62 or selectively to the legs 52 and 54 in a predetermined pattern allowing unambiguous and rapid determination of the orientation and position of the device 50.

The filamentary members 62 may be welded, adhesively bonded or interlaced with the legs 52 and 54 in order to attach the anchoring substrates 58 and 60 to the legs. The anchoring substrates may have any practical shape, such as the flat shape shown in FIG. 4, or the cylindrical, tube or sleeve form coaxially located about the legs 52 and 54 as illustrated in FIGS. 5 and 6.

To aid in initially anchoring the device 50 to living tissue, hooks 68 may be positioned on the legs 52 and 54 distally to the common end point 56. Preferably hooks 68 are co-located with the anchoring substrates 58 and 60 on each leg 52 and 54 and comprise projections which extend outwardly from the legs for engagement with the sidewall of a vessel in which the device 50 is implanted. Hooks 68 engaging the sidewall fix the device 50 in place and allow it to function and provide time for the anchoring substrates 58 and 60 to be integrated with the living tissue of the vessel.

Biasing device 50 is resiliently deformable between a first configuration wherein the legs 52 and 54 are positioned proximally to one another permitting the device to slide through the lumen of a catheter, and a second configuration, illustrated in FIG. 4, where the legs are positioned in spaced relation to one another. Preferably the legs 52 and 54 are resiliently biased to assume the spaced apart configuration in the absence of externally applied constraints, such as are present when the device 50 is within the catheter. This allows the device to expand under the resilient biasing forces and engage the sidewall of the vessel in which it is positioned upon release from a catheter as described below.

FIG. 5 illustrates an alternate embodiment 70 of the biasing device according to the invention. Device 70 has legs 52 and 54 each formed of two segments. Segments 72 and 74, attached together at common end point 56 and oriented angularly with respect to one another comprise first respective segments of legs 52 and 54. Segments 76 and 78, which are respectively attached to segments 72 and 74 comprise the second segments. Segments 76 and 78 extend in substantially parallel, spaced relation to one another when the legs are in the spaced apart configuration illustrated. As shown in detail in FIG. 5A, device 70 has hooks 68 and anchoring substrates such as 58, formed of filamentary members 62, braided or woven into a tubular sleeve and forming interstices 64 to promote the ingrowth of living cells to anchor the device 70 in living tissue. Anchoring substrate 60 is similar and not shown in detail. Referring again to FIG. 5, the leg segments 72 and 74 are attached to one another by a stress relief loop 80 positioned at the common end point 56. Stress relief loop 80 has a predetermined radius of curvature 82 which, by virtue of its shape, reduces the stresses in the leg segments 72 and 74 when they are deformed into the configuration wherein the legs are positioned proximately to one another.

FIG. 6 shows yet another embodiment 84 of the biasing device according to the invention. Instead of being integrally attached to one another at the common point 56, legs 52 and 54 are welded to one another by a weldment 86.

FIGS. 7 through 9 illustrate further embodiments 88, 90 and 92 of the device according to the invention. Embodiment 88, shown in FIG. 7, has legs 52 and 54 each divided into three segments. First segments 94 and 96 are integrally attached together at a first common end point 98. Second segments 100 and 102 are attached, respectively, to ends of first segments 94 and 96 and are oriented in parallel, spaced relation to one another. The anchoring substrates 58 and 60 and hooks 68 are preferably located on the second leg segments 100 and 102. Third leg segments 104 and 106 are attached, respectively, to second leg segments 100 and 102 and are integrally attached to one another at a second common point 108. Together the leg segments 94, 96, 100, 102, 104 and 106 form a closed loop 110.

Embodiment 90, shown in FIG. 8, has angularly oriented leg segments 112 and 114 connected to one another at a common end point 116. A stress relief loop 118 having a predetermined radius 120 is located at the common end point 116 and joins the leg segments 112 and 114. Parallel oriented leg segments 122 and 124 are attached to the ends of angularly oriented leg segments 112 and 114 respectively. Anchoring substrates 126 and 128 are positioned on parallel oriented leg segments 122 and 124 respectively, and hooks 130 are co-located with the anchoring substrates. Another pair of angularly oriented leg segments 132 and 134 extend, respectively, from parallel oriented segments 122 and 124, the angularly oriented leg segments 132 and 134 being attached to one another at another common end 136, for example, by welding, to form a closed loop 138.

FIG. 9 illustrates another embodiment 92 of the device according to the invention. Embodiment 92 comprises angularly oriented leg segments 140 and 142 joined to one another at a common end point 144, for example, by welding. Parallel oriented leg segments 146 and 148 extend respectively from angular leg segments 140 and 142. Anchoring substrates 150 and 152 are positioned on parallel oriented leg segments 146 and 148 along with co-located hooks 154. Second angularly oriented leg segments 156 and 158 extend from the parallel oriented leg segments 146 and 148 respectively and are joined to one another at a second common end point 160, forming a closed loop 162.

As shown in FIGS. 10–15, it may be advantageous to position a shroud, shown in various embodiments 188, 190 and 192, around the biasing device, the particular form, construction and shape of the shroud depending upon the particular function which the biasing device is intended to serve. By way of example, biasing device embodiments 88, 90 and 92 are shown respectively with shroud embodiments 188, 190 and 192, it being understood that any of the shroud embodiments could be used with any of the device embodiments, including embodiments 50, 70 and 84 (see FIGS. 4–6), as well as any device embodiments not specifically illustrated.

Shrouds 188, 190 and 192 preferably comprise interlaced filamentary members 194 which surround the biasing device. Interlacing of the filamentary members may be by weaving, knitting or braiding. The filamentary members may also comprise non-woven constructions such as felts. Continuous, flexible membranes having a wide range of porosity may also be used to form the shroud.

When intended for implantation in living tissue the filamentary members comprise bio-compatible materials such as polyester, polytetrafluoroethylene, nylon, polypropylene, polyethylene and may also comprise metals such as stainless steel, as well as shape memory metals such as nitinol, titanium and stainless steel alloys such as chronochrome, elgiloy and MP35N which expand to a predetermined shape when heated within the body. Bio-absorbable materials such as polylactic acid, polyglycolic acid and HCA are also feasible as filamentary members comprising the shroud. Similarly material candidates for a continuous membrane shroud include expanded polytetrafluoroethylene as well as silicone membranes, polyurethane and laser slotted tubing (described below).

Choice of material is dictated by the function of the shroud. If, for example, the shroud is intended to promote healing and ingrowth of living tissue in order to permanently seal a cavity, such as an atrial appendage, or an opening in a tissue wall, such as a septal defect, or a vessel, such as a blood vessel at the base of an aneurysm, then the preferred material is polyester which promotes an aggressive healing reaction. The filamentary members may also be coated with compounds such as thrombin, collagen, hyaluron or growth factors previously mentioned which promote clotting and cell growth.

If, however, the shroud is to act as a constricting device to control flow through a vessel for example, then materials such as polytetrafluoroethylene are preferred because they will not allow foreign matter to accumulate and form a blockage of the vessel.

FIG. 10 shows an embodiment of shroud 188 on biasing device 88 (see also FIG. 7). Shroud 188 is attached by looping the filamentary members 194 around the leg segments 94–106. The leg segments could also be interbraided or interwoven with the filamentary members. As best shown in FIG. 11, a single central layer 196 spans the loop 110 defined by leg segments 94–106. The single layer center embodiment exemplified by shroud 188 is preferred when an opening or vessel is to be sealed, as the single central layer 196 provides a matrix promoting the intergrowth of living tissue which will join the sides of an opening or vessel together when they are brought into apposition against the single central layer 196 by the biasing device 88.

FIG. 12 illustrates another shroud embodiment 190 positioned on biasing device 90 (see also FIG. 8). Shroud 190 is preferably formed of filamentary members 194 which are woven, braided, or knitted into a tubular sleeve 198 which surrounds the leg segments 112, 114, 122, 124, 132 and 134. The cross sectional view shown in FIG. 13 best illustrates the relation between the sleeve 198 and the leg segments. Shroud 190, in the form of a tubular sleeve is used to advantage when correcting an incompetent valve in a blood vessel. If the biasing device 90 were unshrouded then the leg segments exposed to the blood stream would be a locus for the formation of blood clots which would break away and possibly cause a stroke. The shroud 190 provides a matrix onto which blood cells can attach themselves and eventually encapsulate the biasing device within living tissue. Thus encapsulated, the legs of the device no longer engender a clotting response, thus minimizing or even eliminating the potential for blood clots and stroke.

FIG. 14 shows a shroud 192 comprising a substantially form fitting bag 200 in which the biasing device 92 is sealed (see also FIG. 9). The bag 200 spans the closed loop 162 defined by the leg segments forming the biasing device 92. As best shown in FIG. 15, the bag 200 presents two central layers 202 and 204 positioned in spaced relation on opposite sides of the device 92.

Exemplary Descriptions of the Device in Use

Various examples showing a device according to the invention in use are provided below. It is understood that no limitations are stated or implied by the particular embodiment shown or the particular use for which it is employed.

EXAMPLE 1

Mitral Valve Repair

Figure 16:
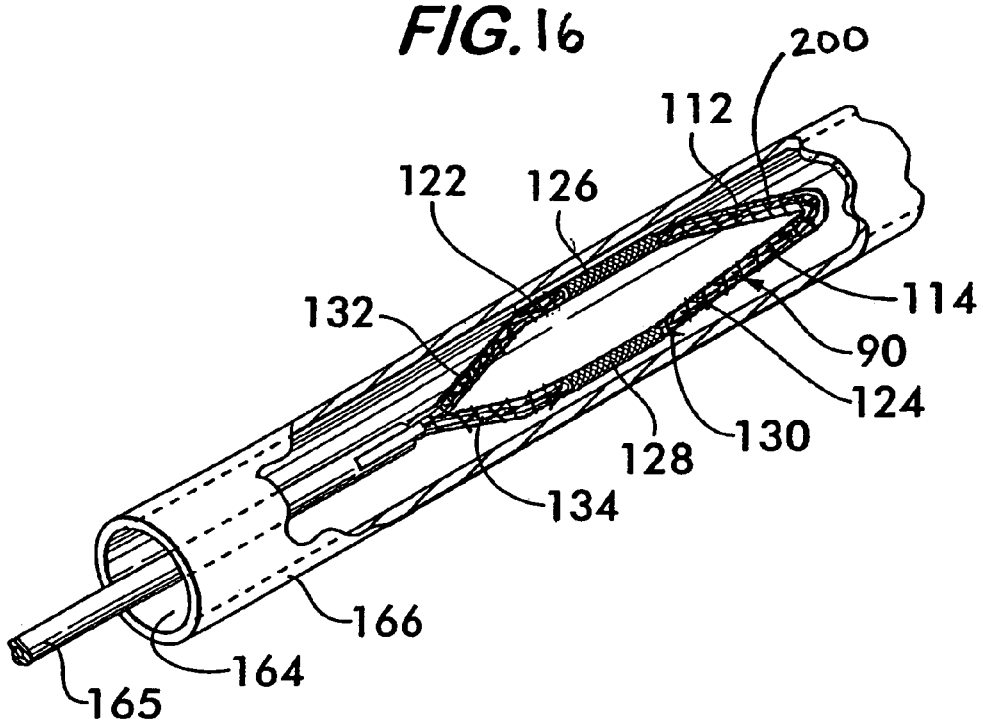
FIG. 16 is a partial cut-away perspective view showing a biasing device according to the invention within a catheter for delivery into a vessel within a body.

FIG. 16 shows biasing device 90 contained within shroud 190 in the form of sleeve 198 in a resiliently deformed configuration with leg segments 112, 122 and 132 positioned proximally to leg segments 114, 124 and 134 allowing device 90 to fit within and slide through a lumen 164 of a catheter 166. Device 90 is resiliently biased to assume the configuration shown in FIG. 8 with the leg segments 112, 114 and 132 in spaced relation to the leg segments 114, 124 and 134. Device 90 will assume this spaced apart configuration upon release from catheter 166, the catheter providing the restraining force to keep the leg segments in the resiliently deformed, proximal configuration. These resilient characteristics of the device allow it to be transported through the vascular system via the catheter to the position where it is to be implanted without the need for traumatic, invasive surgery. The device according to the invention is then released from the catheter by known methods, for example, using a push rod 165, to assume its spaced-apart configuration and biasing the flexible sidewall of a vessel in which it is positioned.

Figure 17:
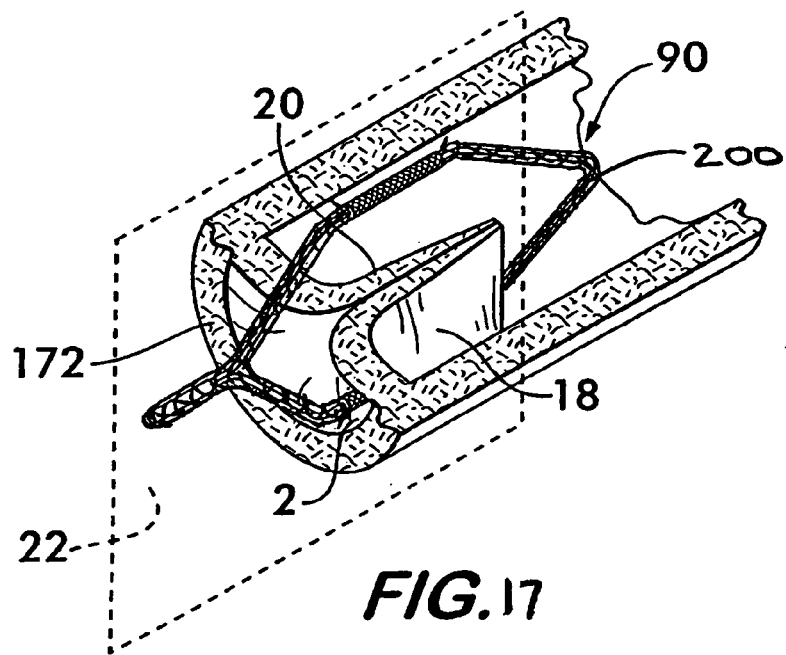
FIG. 17 is a perspective sectional view of a biasing device according to the invention positioned within a valve.

FIGS. 1, 1A and 17 show device 90 positioned within the heart 10 to repair a regurgitating mitral valve 2. Device 90 is deployed with its leg segments 112, 114, 122, 124, 132 and 134 substantially coplanar with the plane 22 of valve 2. What is meant by the "plane of the valve" is best illustrated in FIG. 17 which shows a perspective view of the bicuspid mitral valve 2 having leaflets 18 and 20 in apposition, the plane 22 being shown in dashed line as parallel to the leaflets. As best shown in FIG. 1A device 90 is positioned so that anchoring substrates 126 and 128 and hooks 130 engage opposing portions 168 and 170 of the muscular annulus 172 from which the leaflets 18 and 20 extend. Device 90 is sized and provided with a spring rate so that it biases the opposing annulus portions 168 and 170 outwardly in the plane 22 of the valve. Because the mitral valve 2 acts as a vessel having a flexible sidewall the biasing of opposing annulus portions 168 and 170 outwardly draws leaflets 18 and 20 inwardly towards one another in a direction perpendicular to the plane 22 of the valve as shown in FIG. 17. With the leaflets 18 and 20 in closer proximity to one another, they will tend to seal effectively when back pressure from the left ventricle 8 is applied. Thus, the blood will be forced through the aorta 16 (see FIG. 1) and to the rest of the body and not flow back into the lungs through the left atrium 6 due to an improperly functioning mitral valve 2. For the mitral valve repair the device 90 may range in size from about 1 to 2 inches in length and have an expanded diameter of 30–40 mm. Spring rates describing the effective biasing force with which the device will stretch the mitral valve range between 2 and 3 lbs/inch. The spring rates are determined by the elastic modulus of the particular material comprising the device, as well as the area moment of inertia of the legs as determined by their cross-sectional shape and area. Note that shroud sleeve 200 prevents the device 90 from becoming a locus of clot formation by allowing the ingrowth of blood cells which eventually encapsulate the device 90.

EXAMPLE 2

Venous Valve Repair

FIGS. 2 and 2A show a biasing device 90 according to the invention implanted in a vein 24 to effect repair of an incontinent venous valve 26. Similar to the repair of the mitral valve, the device 90 is deployed from catheter 166 (see FIG. 10) within the vein 24 with its leg segments coplanar with the plane 22 of the valve 26. As shown in FIG. 2A, opposing portions 174 and 176 of the vein 24 at the valve leaflets 30 and 32 are engaged by the anchoring substrates 126 and 128 to bias the opposing vein portions outwardly thereby drawing valve leaflets 30 and 32 inwardly toward one another in a direction perpendicular to the plane 22 of the valve 26. As shown in FIG. 2, by positioning the leaflets 30 and 32 in closer proximity they are more likely to seal effectively when back pressure, as indicated by arrows 175, is applied within vein 24 by muscles 34. With the otherwise incontinent valve 26 repaired, blood is forced to flow through the vein 24 in the desired direction as indicated by arrow 177.

EXAMPLE 3

Repair of Saccular Aneurysm

FIGS. 3 and 3A show device 90 positioned in a saccular aneurysm 36. Device 90 is deployed from a catheter to position its anchoring substrates 126 and 128 at the neck 46 of the aneurysm 36. The anchoring substrates 126 and 128 engage opposing portions 178 and 180 of the neck 46 and bias them outwardly, thereby drawing opposite neck portions 182 and 184 toward one another perpendicular to the plane of the device 90. The biasing action of the device 90 on the neck 46 of aneurysm 36 constricts the neck as shown in FIG. 3 and reduces the flow of blood into the aneurysm, reducing pressure on the dome 48 and providing a stagnant region at the neck 46 which will encourage clotting and eventually seal off the aneurysm, thereby preventing its rupture. Preferably, device 90 has the shroud embodiment 188 which comprises the single central layer 196. Central layer 196 provides a matrix into which cells from the opposing neck portions 182 and 184 may grow to permanently seal the aneurysm 36 and isolate it from the circulatory system.

Preferred materials for the shroud include monofilaments and multifilament yarns of polyester, which will promote an aggressive healing effect, as well as polypropylene, polytetrafluoroethylene and expanded polytetrafluoroethylene. Wire fabrics comprising titanium, nitinol, stainless steel, platinum and elgiloy are also feasible. Non-woven membranes made from silicone and polyurethane, particularly in the form of slotted tubes, are also contemplated by the invention. As needed, the shroud may be coated with compounds, such as thrombin, collagen, hyaluron and growth factors to promote tissue ingrowth or blood clotting, or antiproliferative drugs such as Taxol, Rapamycin and Rapamune to prevent tissue ingrowth and inhibit tissue adhesion.

EXAMPLE 4

Closure of Atrial Appendage

Figure 1B:
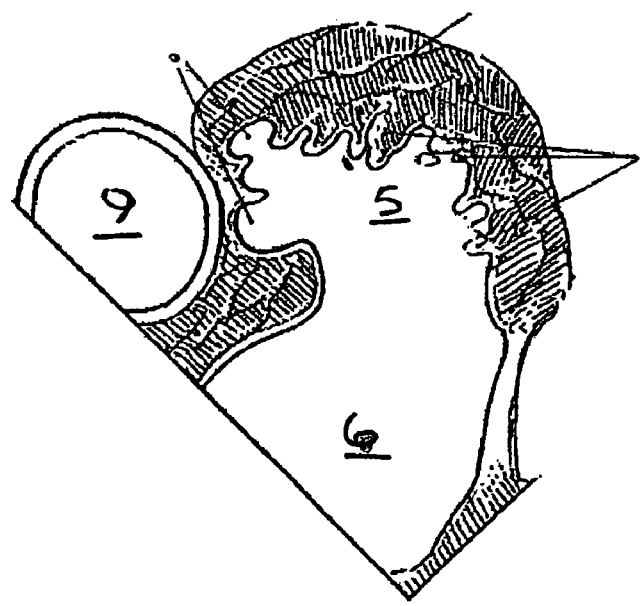
FIG. 1B is a partial sectional view taken at line 1B—1B in FIG. 1 and showing an atrial appendage.
Figure 18:
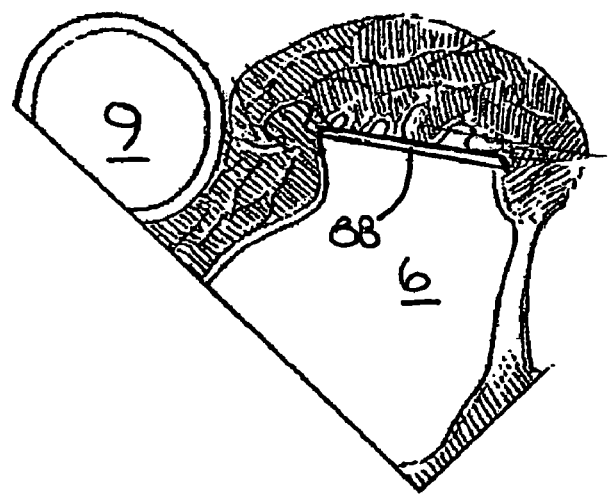
FIG. 18 is a partial cross-sectional view of a biasing device positioned within an atrial appendage.

FIG. 1B illustrates an atrial appendage 5 located in the left atrium 6 adjacent to the pulmonary trunk 9. To effect closure of this appendage 5 a biasing device, for example 88, may be inserted within the atrial appendage 5 as shown in FIG. 18 to collapse the appendage into the atrium 6 and eliminate it as a potential source for blood clots leading to stroke. Biasing device 88 may be inserted via a catheter, thus, providing a minimally invasive technique for correcting this heart defect.

EXAMPLE 5

Treatment of Patent Foramen Ovale and Septal Defects

Figure 1C:
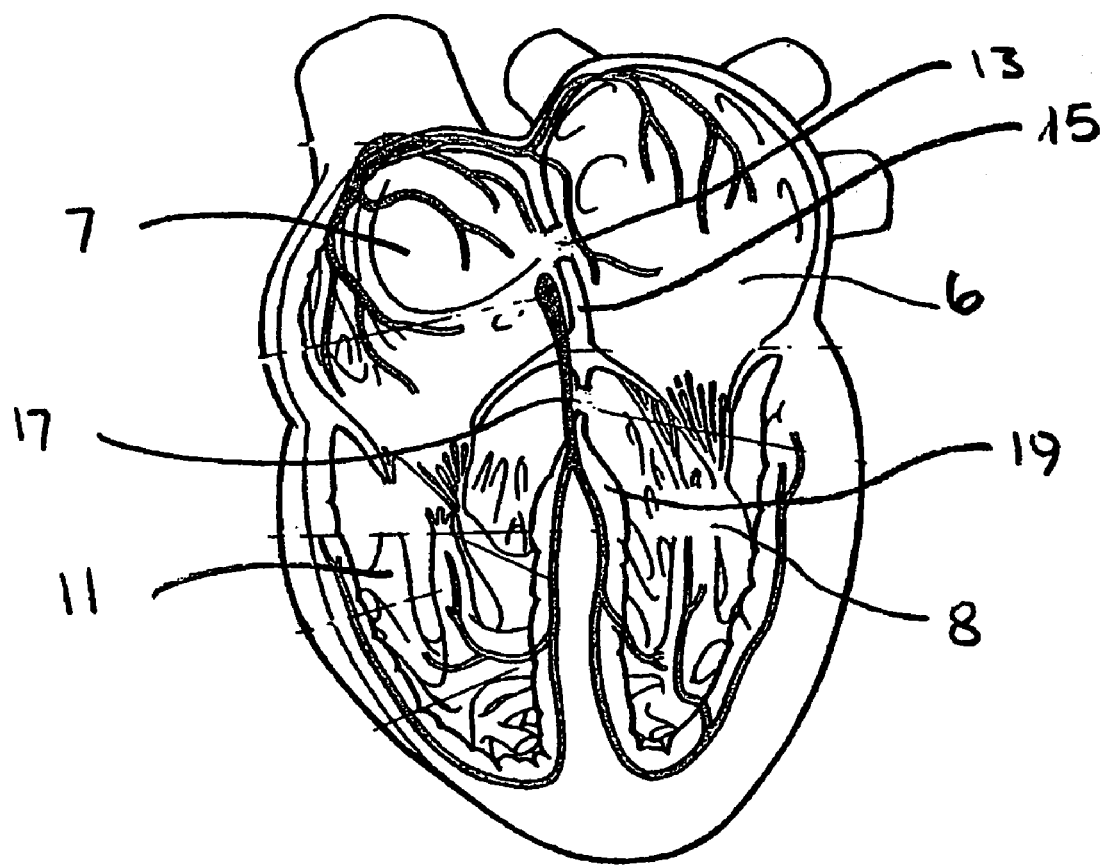
FIG. 1C is a partial sectional back view of a human heart displaying the left and right ventricles and atria.

Defects involving openings in the muscular tissue of the heart which allow abnormal blood flow such as patent foramen ovale (see 3 in FIG. 1) and atrial and ventricular septal defects (13 and 17 in FIG. 1C) may be treated by inserting a biasing device according to the invention into the opening. Inserted using a catheter, the biasing device expands upon release therefrom, either through elastic biasing of the leg segments or by the special properties of shape memory metals which expand upon heating to a predetermined shape. The biasing device stretches the muscle tissue, bringing opposing portions into apposition to contact one another or opposite sides of a shroud layer into which the tissue may grow to permanently seal the opening.

EXAMPLE 6

Control of Fluid Flow

Vessels which conduct fluids other than blood, such as the esophagus, the urethra, and the like are also subject to disorders. For example, one cause of gastroesophageal reflux is a decrease in the resting tone of the lower esophageal sphincter between the esophagus and the stomach. The lower esophageal sphincter allows stomach acid to flow into and damage the esophagus, causing the discomfort commonly known as "heartburn". A leaky sphincter may be tightened by positioning a biasing device according to the invention within its diameter to stretch it and reduce the size of the resting opening to prevent acid reflux.

Bladder incontinence may be treated by positioning a biasing device within the urethral sphincter. The stiffness of the device would be tuned to allow urine to flow in a controlled manner but prevent unwanted leakage.

Birth control methods may also be feasible using the biasing device according to the invention. In females, biasing devices may be implanted within the fallopian tubes to close them and thereby prevent passage of eggs to the uterus. The implantation would be less invasive than a tubal ligation and could also be reversible as the biasing device is thought to be removable under certain conditions.

Similarly, positioning biasing devices in the vas deferens would effectively block the passage of sperm from the testes in males.

Figure 19:
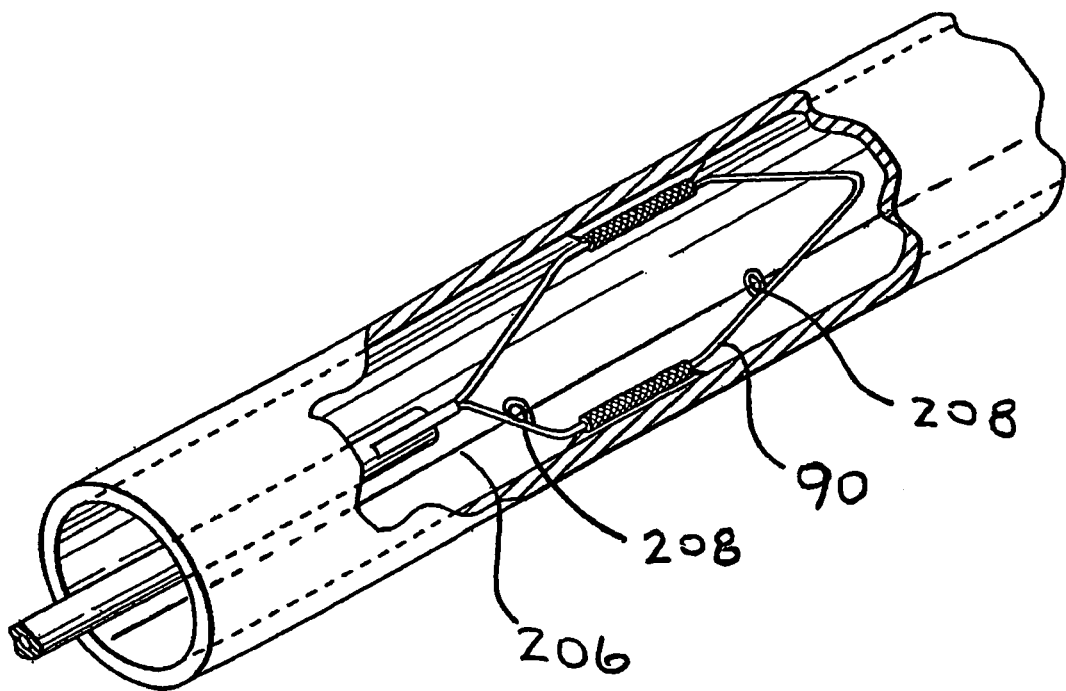
FIG. 19 is a perspective view of a biasing device adapted for delivery by a guide wire.
Figure 20:
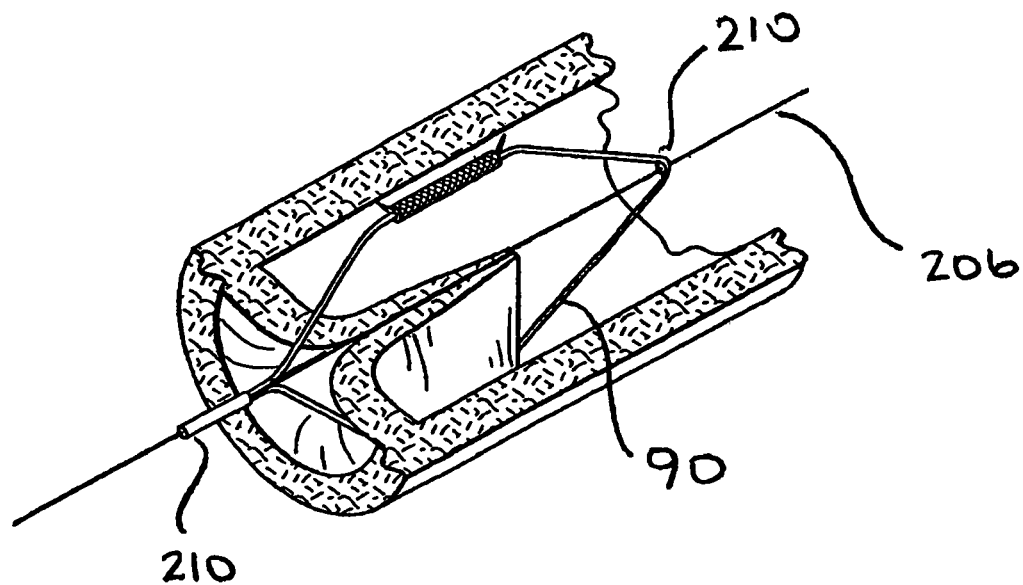
FIG. 20 is a perspective view of an alternative embodiment of a biasing device adapted for delivery by a guide wire.

The various embodiments of the biasing device described above and depicted in the Figures may be delivered over a guide wire when advantageous. FIGS. 19 and 20 show examples of embodiment 90 adapted for delivery on a guide wire 206. As shown in FIG. 19, embodiment 90 has lugs 208, mounted offset from the centerline of the device to engage guide wire 206 and allow the device 90 to slide over it for precise and convenient positioning. In FIG. 20, device 90 has apertures 210, in this example, positioned along the device centerline, which receive the guide wire 206 and allow precise sliding motion of the device along the path defined by the guide wire.

Figure 21:
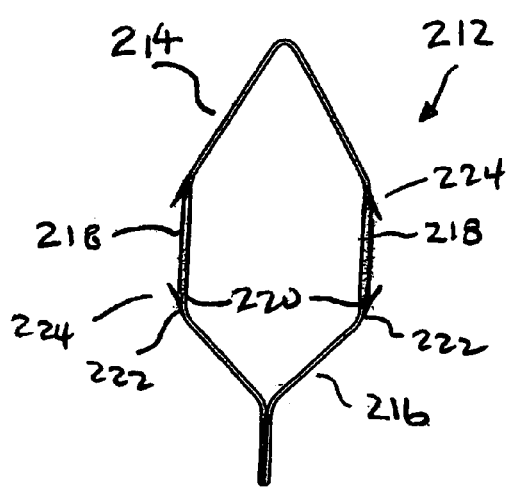
FIGS. 21 and 22 are plan views of a removable embodiment of a biasing device according to the invention.
Figure 22:
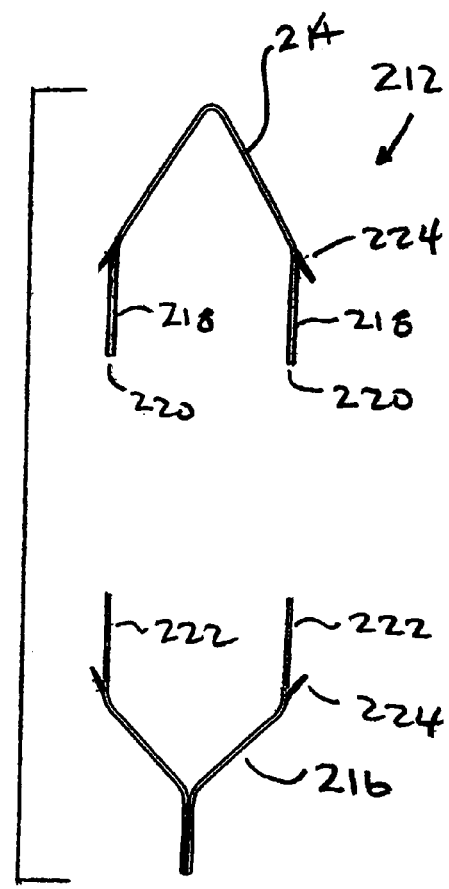
Figure 23:
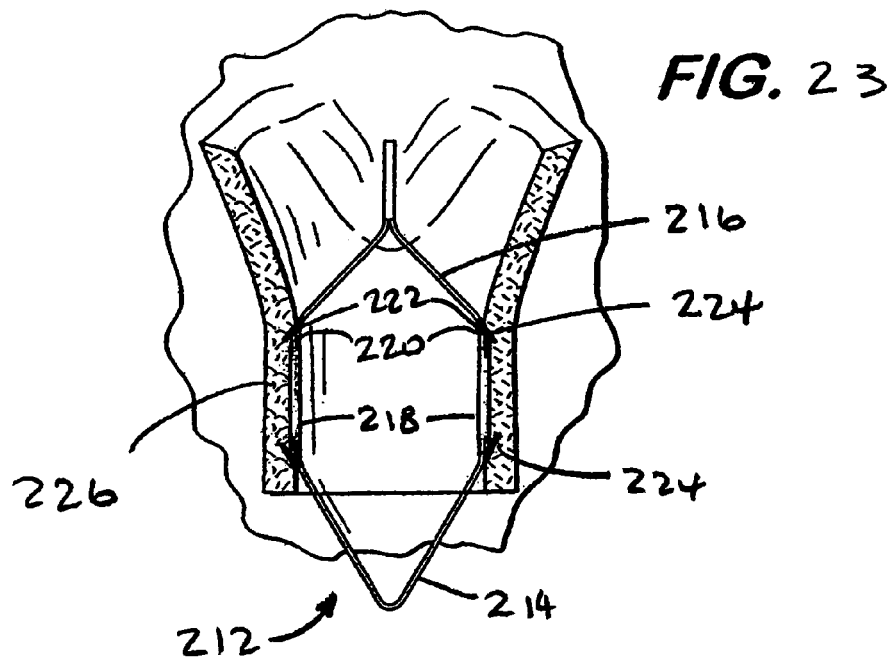
FIGS. 23 and 24 show the device of FIG. 21 being removed from flexible tissue.
Figure 24:
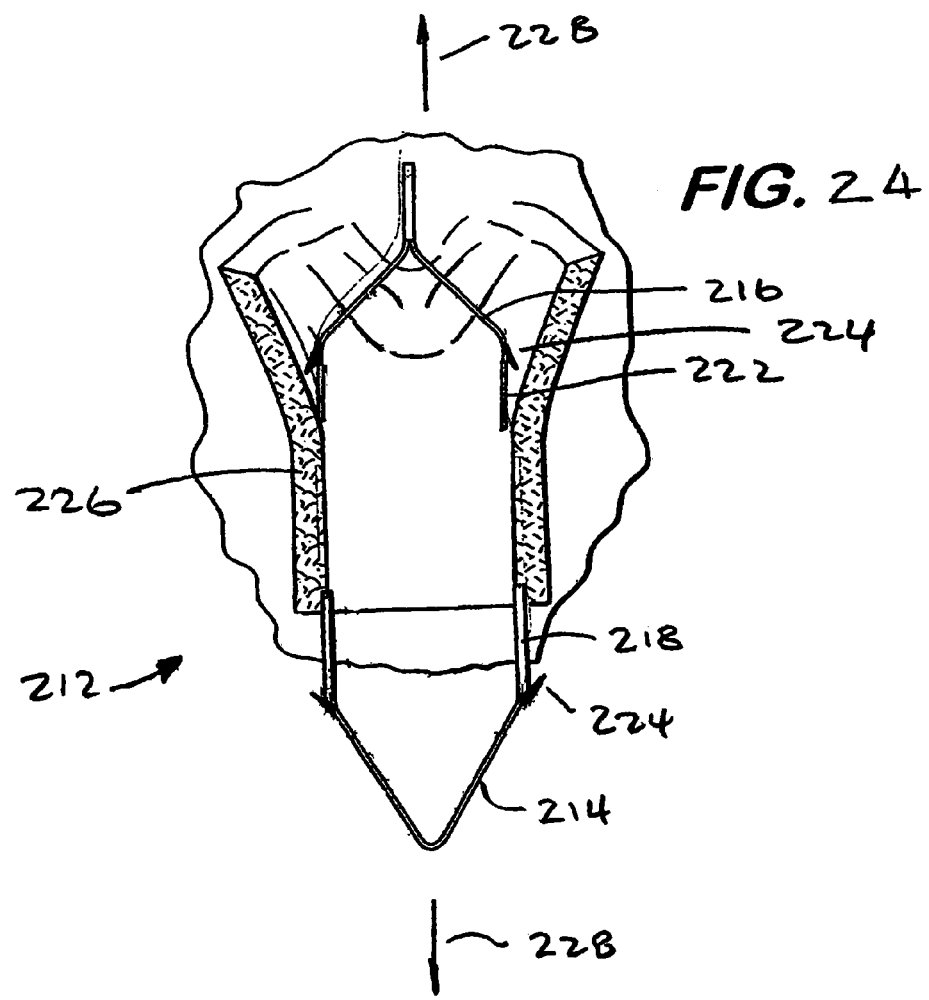

The device according to the invention may also be adapted to be removably positioned within a flexible walled vessel or in an opening in soft tissue. FIGS. 21 and 22 show an embodiment 212 of a removable device according to the invention. Device 212 preferably comprises two separable components which may, for example, be formed from an upper portion 214 and a lower portion 216. Upper portion 214 has segments 218 with respective bores 220 adapted to receive interfitting segments 222 extending from the lower portion 216. Segments 222 may be held within bores 220 by friction, or adhesive, or by interlocking or detent means to keep the upper and lower portions 214 and 216 together as shown in FIG. 21, but allow them to be separated from one another, as shown in FIG. 22, by the application of sufficient predetermined force. Device 212 preferably has barbs 224 on each of the upper and lower segments 214 and 216. For the removable embodiment the barbs 224 point toward each other inwardly in relation to the device 212. As shown in FIG. 23, such a barb orientation prevents motion of device 212 within a vessel 226 or other soft tissue as long as both upper portion 214 and lower portion 216 remain together and both portions are moved in the same direction. However, as shown in FIG. 24, if the upper and lower portions 214 and 216 are moved in opposite directions away from one another as indicated by arrows 228, which will tend to separate them from one another, then the barbs 224 no longer provide resistance to motion but, because of their inwardly angled orientation, will slide over the soft tissue and permit the upper and lower portions to be separated from one another and removed from the vessel or tissue in which they were originally implanted.

As an alternative, the biasing device according to the invention may be made from a thin-walled tube. Preferably, the tube comprises a shape-memory metal such as nitinol or elgiloy although other metals having significant resilience and a high yield strength, such as stainless steel and titanium are also feasible.

Figure 25:
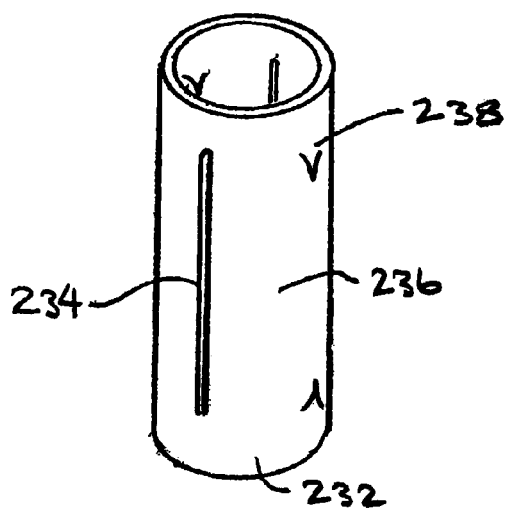
FIGS. 25 and 26 are perspective views of an alternate embodiment of a biasing device being prepared from a tube.
Figure 26:
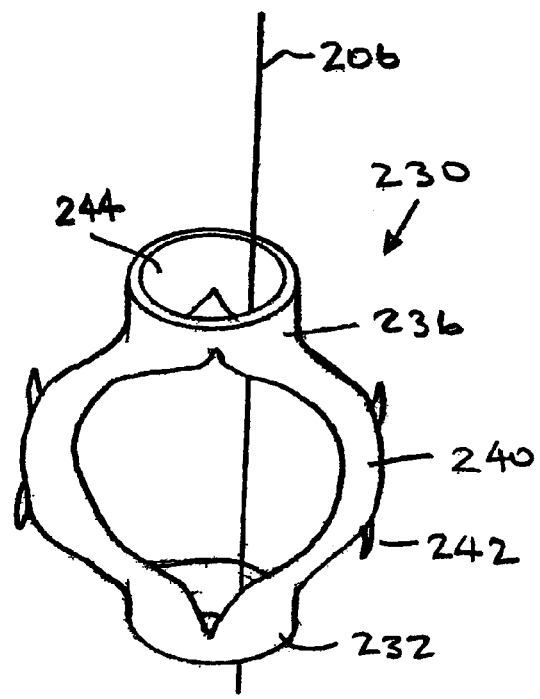

FIGS. 25 and 26 show a biasing device embodiment 230 prepared from a thin walled tube 232. As shown in FIG. 25, slots 234 are formed in the tube wall 236 opposite to one another. The slots may be formed by laser cutting as well as by using a saw or knife blade. V-shaped cuts 238 are further formed through the tube wall 236 opposite to each other and at 90° circumferentially around the tube from the slots 234. The device 230 as shown in FIG. 26 is prepared by expanding the tube 232 outwardly so as to open slots 234, the tube wall 236 between the slots forming the segments 240 for engaging and biasing or distending the vessel or tissue in which the device is implanted. Expansion of the tube 232 is preferably done over a mandrel with the application of heat to bias the device into the expanded shape shown in FIG. 26. Due to the flexible, resilient nature of the material forming the tube the device may be deformed substantially back into a tubular shape so as to slide within a catheter and then expand upon release from the catheter into the shape shown in FIG. 26. Alternately, the device may have the tubular shape of FIG. 25 as its nominal shape and be yieldably expanded outwardly after implanting by a balloon. The V-shaped cuts 238 form hooks 242 extending outwardly from segments 240, the hooks being engageable with soft tissue to fix the device in position as described for previous embodiments. The tube, by virtue of its bore 244 defined by the tube wall 236 may be conveniently guided by a guide wire 206 for precise positioning.

Figure 27:
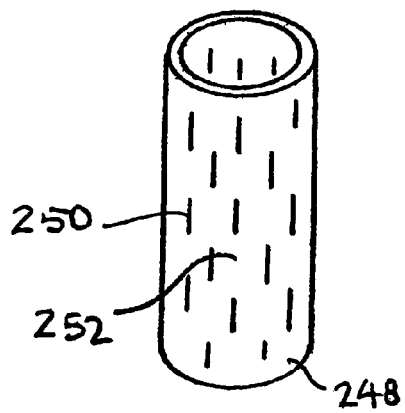
FIGS. 27 and 28 are perspective views of another embodiment of a biasing device prepared from a tube.
Figure 28:
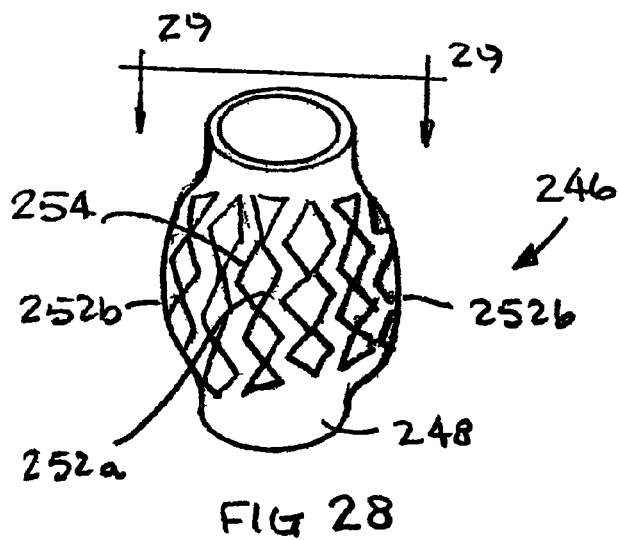
Figure 29:
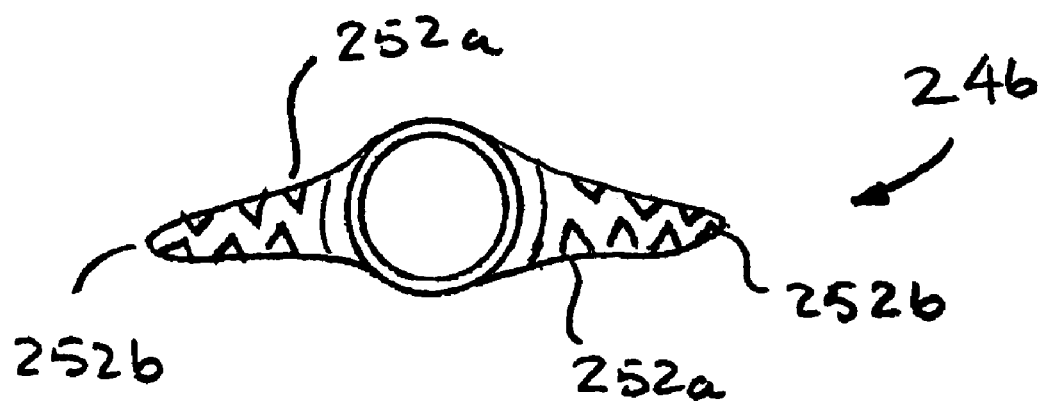
FIG. 29 is an end view taken at line 29—29 from FIG. 28.

FIGS. 27 and 28 show another embodiment of a device 246 formed from a tube 248. Tube 248 has a plurality of slots 250, preferably asymmetrically formed on opposite sides of the tube wall 252, i.e., the slots are not distributed circumferentially around the tube. The asymmetrical distribution of the slots forces the tube to expand in a flattened shape, best shown in FIG. 29, with the opposite slotted sides 252a of the tube being drawn together when the regions 252b, positioned adjacent to the slotted regions, are drawn apart. The slots 250 may be arranged, interconnected and shaped to form a particular complex pattern 254 (shown in FIG. 28) when the tube 248 is expanded. The pattern may form a matrix promoting the ingrowth of cells, or may provide a lattice structure providing stiffness and strength for biasing the vessel wall or tissue opening outwardly.

Figure 30A:
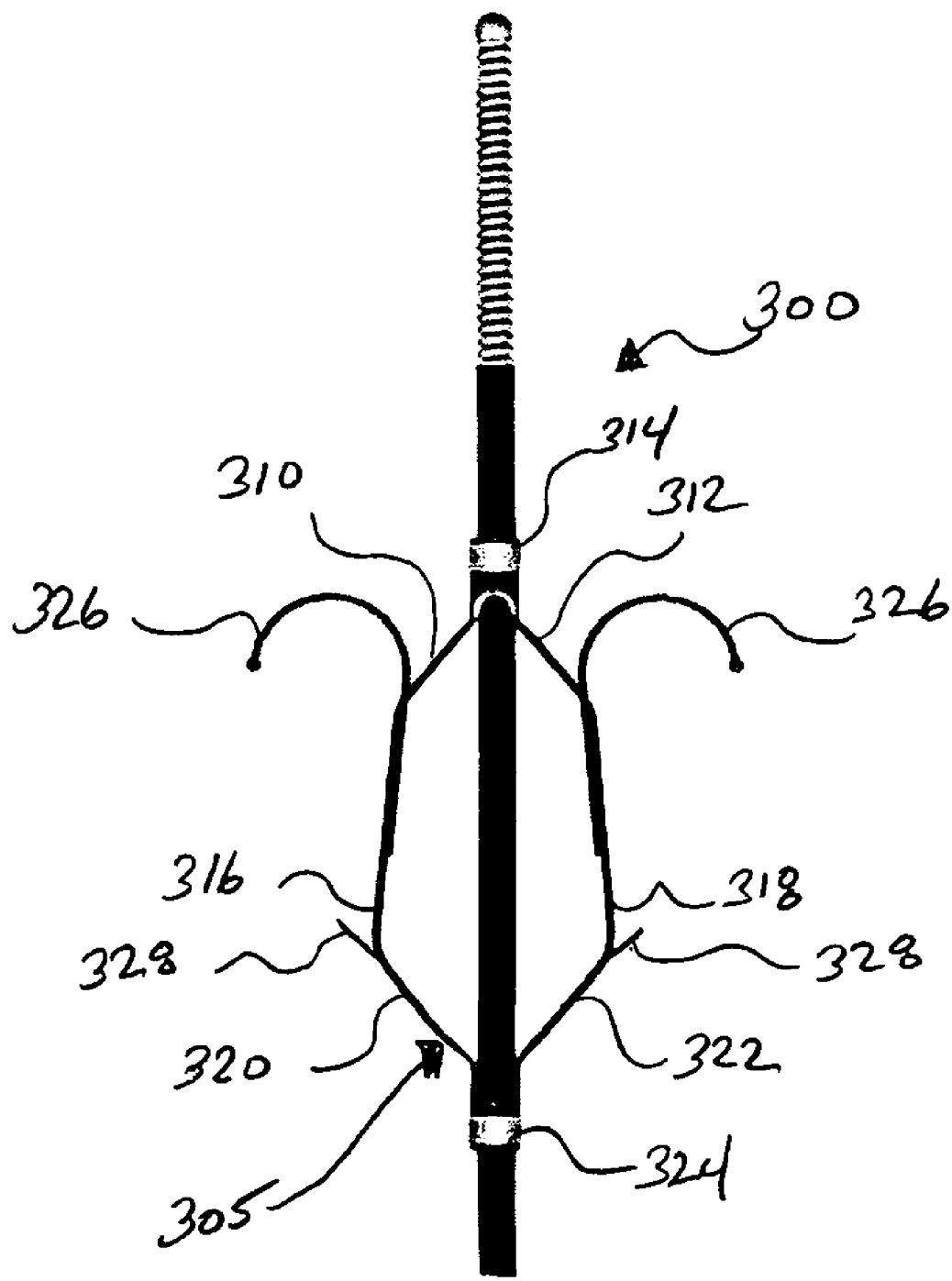
FIG. 30 is a perspective view of the frame of another embodiment of a biasing device.
Figure 30B:
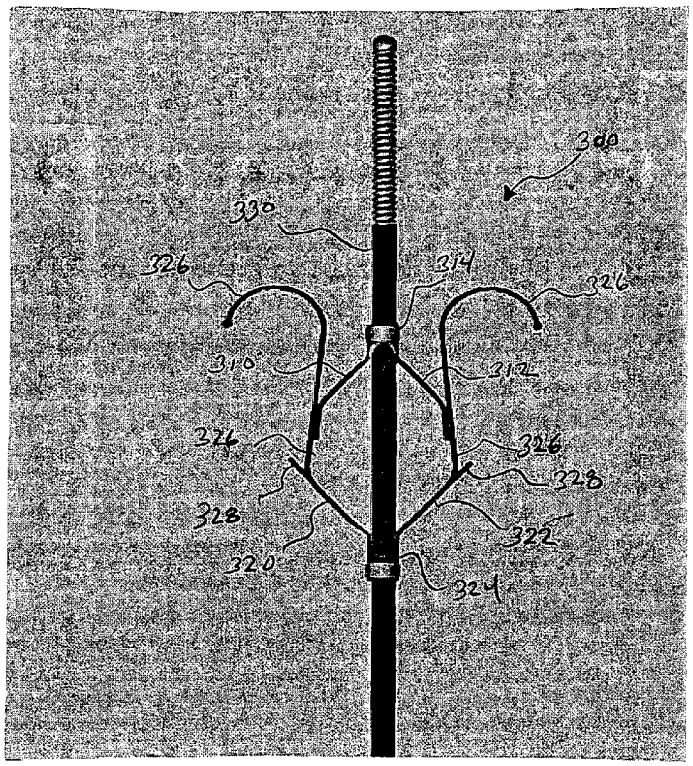

FIGS. 30A–B show a preferred biasing device 300, particularly suitable for treating a patent foramen ovale. As shown in FIG. 30A, device 300 has includes a frame 305 comprised of a plurality of leg segments. A first set of angularly oriented leg segments 310 and 312 are resiliently connected to a first collar member 314. A second set of leg segments 316 and 318 are attached to and angled outwardly from the ends of leg segments 310 and 312. Leg segments 310 and 312 are attached to a third set of leg segments 320 and 322, which are angled inwardly from the point of attachment with leg segments 316 and 318 and resiliently connected to a second collar member 324. Left atrial anchors 326 and right atrial anchors 328 extend beyond frame 305 are provided to anchor the device within the opening defined by the foramen ovale. In a preferred embodiment, as shown in FIG. 30A, left atrial achor 326 is attached to and coextensive with leg segments 316 and 318, respectively, in the direction of first collar member 314, and includes a hook portion 317 formed at its end proximal to first collar member 314. Right atrial anchor is attached to and coextensive with end of leg segments 320 and 322 distal to second collar member 324. Both left atrial anchors 326 and right atrial anchors 328 extend beyond frame 305. Left atrial anchors are preferably are covered by tantalum coil 329 over nitinol wire (not shown), to improve radiocapacity. Further, first collar member 314 and second collar member 324 preferably include tantalum markers or a tantalum coating to improve radiocapacity.

In an alternative embodiment, as shown in FIG. 30B, leg segments 310 and 312 are attached to a portion of left atrial anchors 326 located distally from the hooked end, which in turn is attached by, e.g. welding, to leg segments 320 and 322 proximal to the outwardly extending ends of right atrial anchors 328.

Figure 30C:
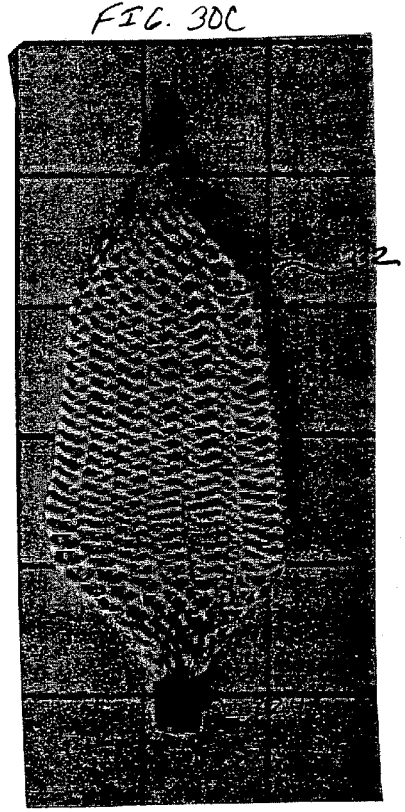

In one embodiment, frame 305 of biasing device is covered with a shroud 332, as shown in FIG. 30C, the possible make and construction of which is described above. The shroud is intended to promote healing and ingrowth of living tissue in order to permanently seal a cavity. The preferred material is polyester which promotes an aggressive healing reaction. As described above, the filamentary members may also be coated with compounds such as thrombin, collagen, hyaluron, or growth factors previously mentioned which promote clotting and cell growth.

Biasing device 300 is resiliently deformable to permit the device to slide through the lumen of a catheter. When, for example, leg segments 316 and 318 are biased toward one another, first collar member 314 and second collar member 324 are forced in opposite directions as the width of the frame 305 narrows. As biasing device 300 is removed from the catheter, frame 305 expands to its predetermined width. To facilitate placement of device 300, a guide wire 330 can be fed through the center of first collar member 314 and second collar member 324.

When treating a patent foramen ovale, for example, the distal end of a catheter tube, within which device 300 is inserted, is extended, from the direction of the right atria to the left atria, through the opening defined by the foramen ovale, such that the distal end of the catheter extends slightly into the left atria. Using a push tube, for example, device 300 is pushed out the catheter's distal end and manipulated such that hook portions 317 of atrial anchors 324 engage the tissue of the left atria surrounding the opening and such that right anchors 328 are forced against right atrial tissue adjacent to the opening. As device 300 is removed from the opening, the width of frame 305 will expand so as to distend the tissue surrounding the opening.

The biasing device according to the invention provides a versatile article for repairing openings in tissue, anomalies in vessels having flexible sidewalls, as well as controlling the flow of fluid through such vessels and may be employed to cure or repair disorders of the circulatory system as well as other systems in the body with minimally invasive surgical techniques thereby avoiding unnecessary trauma to the patient.

What is claimed is:

1. A biasing device positionable within a body opening defined by a flexible sidewall, said biasing device having a first deformed configuration to facilitate insertion through a catheter and being automatically expandable toward a second configuration when released from said catheter, the biasing device comprising:

at least first and second side wall engaging members operable to respectively engage and outwardly expand opposed portions of the sidewall on opposite sides of the opening during expansion of said biasing device to an operable position, wherein the first side wall engaging member is closer to the second side wall engaging member in the first configuration than in the second configuration, and said at least first and second side wall engaging members being substantially coplanar when expanding from the first configuration to the second configuration, wherein the first side wall engaging member has at least four bends, and wherein the second side wall engaging member has at least four bends; and at least one expandable and contractible joinder member connected between the said first and second sidewall engaging members, said joinder member being formed to contract to position said at least first and second sidewall engaging members proximate to one another for insertion in a catheter and to expand upon release of said biasing device from said catheter; and a shroud covering the first and second side wall engaging members and extending between the first and second side wall engaging members;

wherein the first side wall engaging member comprises a first anchoring mechanism protruding in a first direction from a remainder of the first side wall engaging member, wherein the first direction is coplanar with the first and second side wall engaging members; and wherein the first anchoring mechanism comprises at least one or more hooks; and wherein the biasing device defines a substantially flat shape.

2. The biasing device of claim 1, further comprising a second anchoring mechanism protruding in a second direction from the second side wall engaging member, wherein the second direction is coplanar with the first and second side wall engaging members.

3. The biasing device of claim 2, wherein the shroud comprises a plurality of interlaced filamentary members defining a plurality of interstices between said filamentary members.

4. The biasing device of claim 3, wherein said plurality of interstices are sized to promote the intergrowth of living tissue onto the anchoring substrates.

5. The biasing device of claim 3, wherein said filamentary members are coated with at least one of thrombin, collagen, hyluron and a host growth factor.

6. The biasing device of claim 3, wherein the filamentary members comprise a metal.

7. The biasing device of claim 6, wherein said metal is gold.

8. The biasing device of claim 3, wherein said shroud is formed of a metal.

9. The biasing device of claim 8, wherein said metal is at least one of a shape memory metal or a stainless steel alloy.

10. The biasing device of claim 3, wherein the shroud is coated with at least one of thrombin, collagen, hyaluron or a host growth factor.

11. The biasing device of claim 3, wherein said filamentary members comprise a radiopaque material.

12. The biasing device of claim 11, wherein said radiopaque material is selected from the group consisting of gold, barium and titanium.

13. The biasing device of claim 3, wherein said filamentary members have a radiopaque coating.

* * * * *